United States Patent [19]

Guilbeau et al.

[11] Patent Number: 4,935,345

[45] Date of Patent: Jun. 19, 1990

[54] IMPLANTABLE MICROELECTRONIC BIOCHEMICAL SENSOR INCORPORATING THIN FILM THERMOPILE

[75] Inventors: Eric J. Guilbeau, Tempe; Bruce C. Towe, Mesa, both of Ariz.

[73] Assignee: Arizona Board of Regents, Tempe, Ariz.

[21] Appl. No.: 142,297

[22] Filed: Dec. 30, 1987

Related U.S. Application Data

[63] Continuation of Ser. No. 35,197, Apr. 7, 1987, abandoned, which is a continuation of Ser. No. 894,757, Aug. 13, 1986, abandoned, which is a continuation of Ser. No. 641,566, Aug. 16, 1984, abandoned.

[51] Int. Cl.⁵ .......................... C12Q 1/54; A61B 5/05
[52] U.S. Cl. .......................................... 435/14; 435/4; 435/27; 435/288; 435/290; 435/291; 435/817; 128/635
[58] Field of Search ............... 435/288, 289, 290, 291, 435/817, 25, 27, 14, 4; 128/632, 635; 204/1 T, 403

[56] References Cited

U.S. PATENT DOCUMENTS

| | | | |
|---|---|---|---|
| 3,878,049 | 4/1975 | Tannenbaum et al. | 195/103.5 R |
| 3,972,681 | 8/1976 | Clack et al. | 23/253 R |
| 4,020,830 | 5/1977 | Johnson et al. | 128/2 E |
| 4,021,307 | 5/1977 | Mosbach | 195/103.5 R |

OTHER PUBLICATIONS

Albisser & Spencer, "Electronics and the Diabetic", p. 239, Transactions on *Biomedical Engineering*, vol. BME-29, No. 4, Apr. 1982.

Lawrence Ingrassia, "Medtronic Researchers Try Hard to Develop In-Body Drug Device", Wall Street Journal, Tuesday, Apr. 12, 1983.

Soeldner, "Symposium on Potentially Implanatable Glucose Sensors", *Diabetes Care*, vol. 5, No. 3, May--Jun. 1982, p. 147.

Thevenot, "Problems in Adapting a Glucose-Oxidase Electrochemical Sensor into an Implantable Glucose-Sensing Device", *Diabetes Care*, vol. 5, No. 3, May-Jun. 1982, pp. 184-189.

Kondo, et al., "A Miniature Glucose Sensor, Implantable in the Blood Stream", *Diabetes Care*, vol. 5, No. 3, May-Jun. 1982, pp. 218-221.

Oberhardt et al., "Glucose Sensor Characteristics for Miniaturized Portable Closed-Loop Insulin Delivery: A Step Toward Implantation", *Diabetes Care*, vol. 5, No. 3, May-Jun. 1982, pp. 213-217.

Wolfson, et al., "Glucose Concentration at Possible Sensor Tissue Implant Sites", Diabetes Care, vol. 5, No. 3, May-Jun., 1982, pp. 162-165.

Fulton, Cooney & Weaver, "Thermal Enzyme Probe with Differential Temperature Measurements in a Laminar Flow-Through Cell", *Analytical Chemistry*, vol. 52, No. 3, Mar. 1980, pp. 505-508.

(List continued on next page.)

Primary Examiner—Nam X. Nguyen
Attorney, Agent, or Firm—Cahill, Sutton & Thomas

[57] ABSTRACT

A biochemical sensor is provided for measuring the concentration of a chemical dissolved within a fluid by providing a differential voltage proportional to a temperature differential resulting from the heat evolved from the enzymatic reaction of the chemical under test. The biochemical sensor is formed by depositing thin films of two dissimilar metals upon a substrate using microelectronic fabrication techniques. A multiplicity of thermocouple junctions are created at the intersections of the two dissimilar metal films, and the resulting series-connected thermocouple junctions are alternately designated sensing and reference junctions. The sensing junctions, but not the reference junctions, are covered by an enzyme, catalyst, or other species for initiating a chemical reaction involving the chemical under test, giving rise to a temperature differential between the sensing and reference junctions proportional to the concentration of the chemical under test. The biochemical sensor may be implanted within a human body for continuously monitoring concentrations of glucose or other chemicals present within the bloodstream.

24 Claims, 3 Drawing Sheets

OTHER PUBLICATIONS

Mosbach & Danielsson, "Thermal Bioanalyzers in Flow Streams Enzyme Thermistor Devices", *Analytical Chemistry*, vol. 53, No. 1, Jan. 1981, pp. 83A-94A.

Wunderman & Muray, "Thermopile Detectors for Biomedical Temperature Measurements", *Temperature, Its Measurement and Control in Science and Industry*, Instrument Society of America, Pittsburgh, Pa. 1972, vol. 4, Pt. 3, pp. 2151-2157.

Mosbach & Danielsson, "An Enzyme Thermistor", *Biochimica et Biophysica Acta*, 364 (1974), pp. 140-145.

Mattiasson et al., "A Split-Flow Enzyme Thermistor", *Analytical Letters*, 9(10), 867-889 (1976).

Mosbach, Danielsson, Bogerud and Scott, "Determination of Heat Changes in the Proximity of Immobilized Enzymes with an Enzyme Thermistor and Its Use for the Assay of Metabolites", *Biochimica et Biophysica Acta*, 403 (1975) 256-265.

Weaver et al., "Experiments and Calculations Concerning a Thermal Enzyme Probe", *Biochimica et Biophysica Acta*, 452 (1976) 285-291.

Mattiason et al., "Enzyme Thermistor Assay of Cholesterol, Glucose, Lactose and Uric Acid in Standard Solutions as Well as in Biological Samples", *Analytical Letters*, 9 (3), 217-234 (1976).

Kuu & Polack, "Improving Immobilized Biocatalysts by Gel Phase Polymerization", *Biotechnology and Biooengineering*, vol. XXV, pp. 1995-2006 (1983).

Angell, Terry & Barth, "Silicon Micromechanical Devices", *Scientific American*, Mar. 1983, pp. 44-55.

Osborn et al., "Use of Chemically Modified Activated Carbon as a Support for Immobilized Enzymes", *Biotechnology and Bioengineering*, vol. XXIV, pp. 1653-1669 (1982).

Lahiji and Wise, "A Batch-Fabricated Silicon Thermopile Infrared Detector", *IEEE Transactions on Electron Devices*, vol. Ed-29, No. 1, Jan. 1982, pp. 14-22.

Guilbeau & Mayhall, "Microthermocouple for Soft Tissue Temperature Determination", *IEEE Transactions on Biomedical Engineering*, vol. BME-28, No. 3, Mar. 1981, pp. 301-305.

Guilbault, "Future of Biomembrane Probes", *Theory, Design and Biomedical Applications of Solid State Chemical Sensors*, CRC Press, 1978, pp. 193-204.

Lahiji, "A Monolithic Thermopile Detector Fabricated Using Integrated Circuit Technology", Ph.D. Dissertation, Dept. of Elec. & Comp. Engr., Stanford University, Jun. 1981.

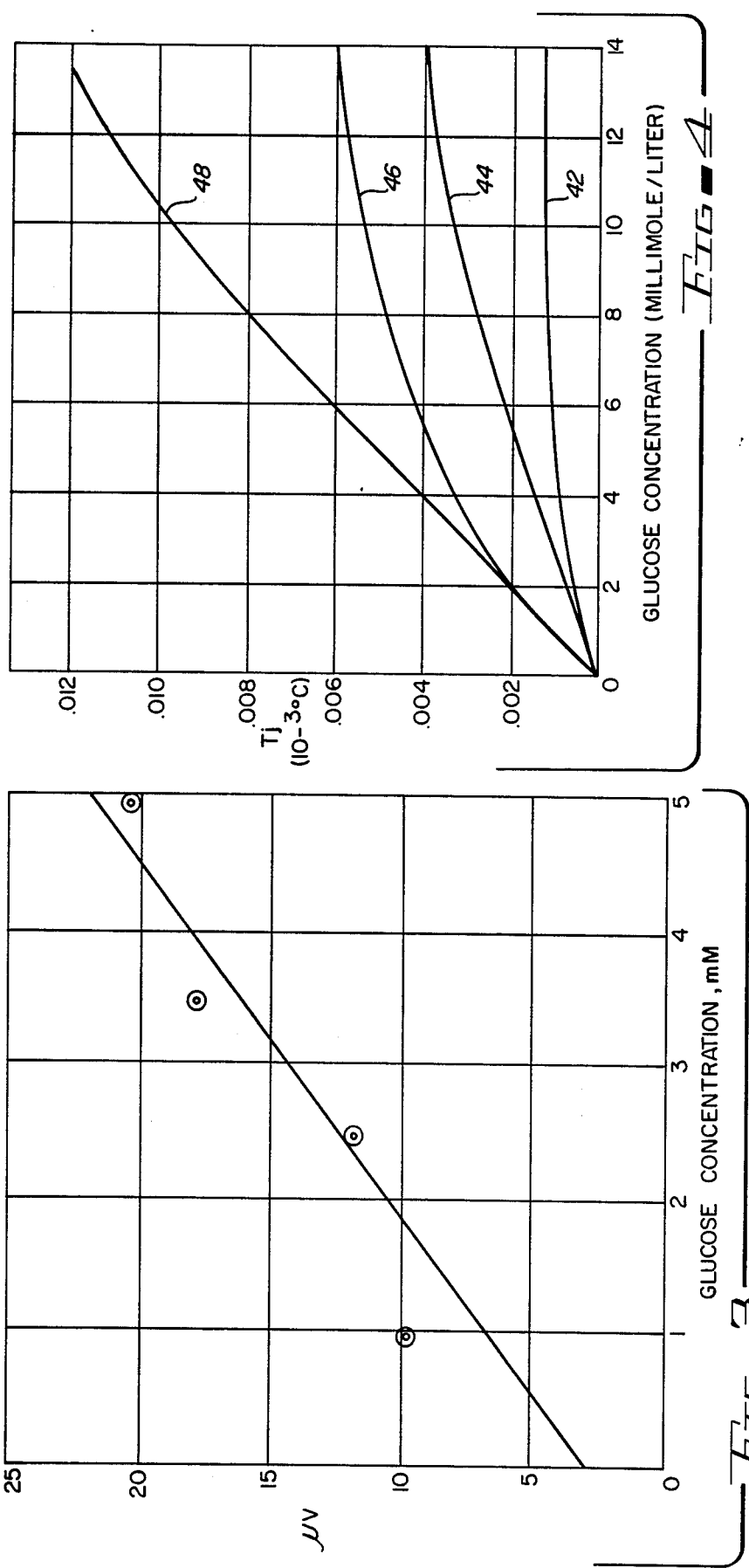
FIG_4
FIG_3
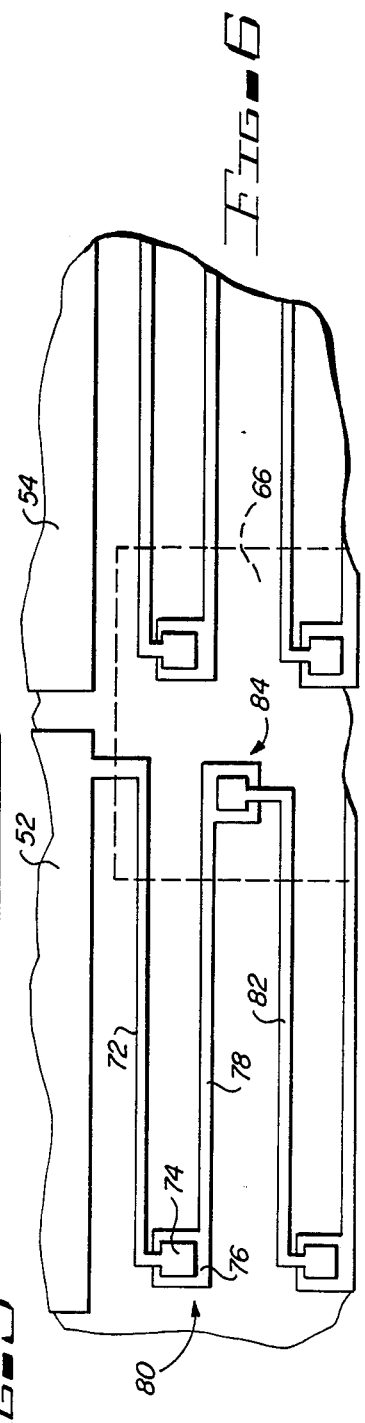
FIG_6

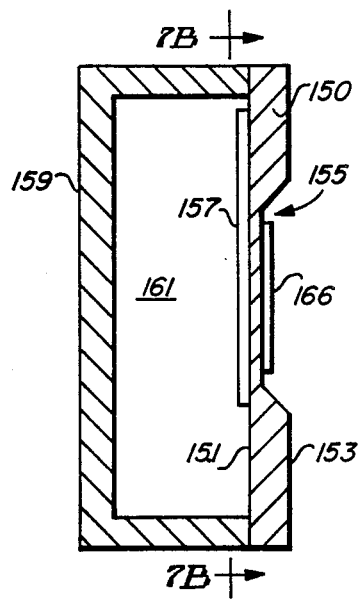
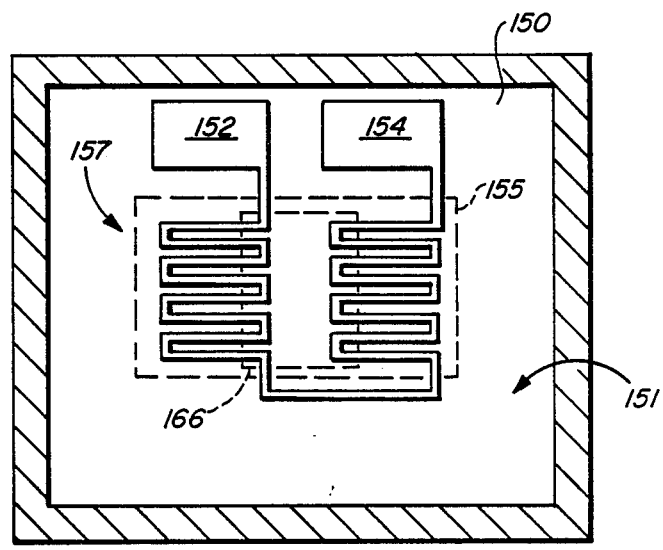
Fig-7A  Fig-7B
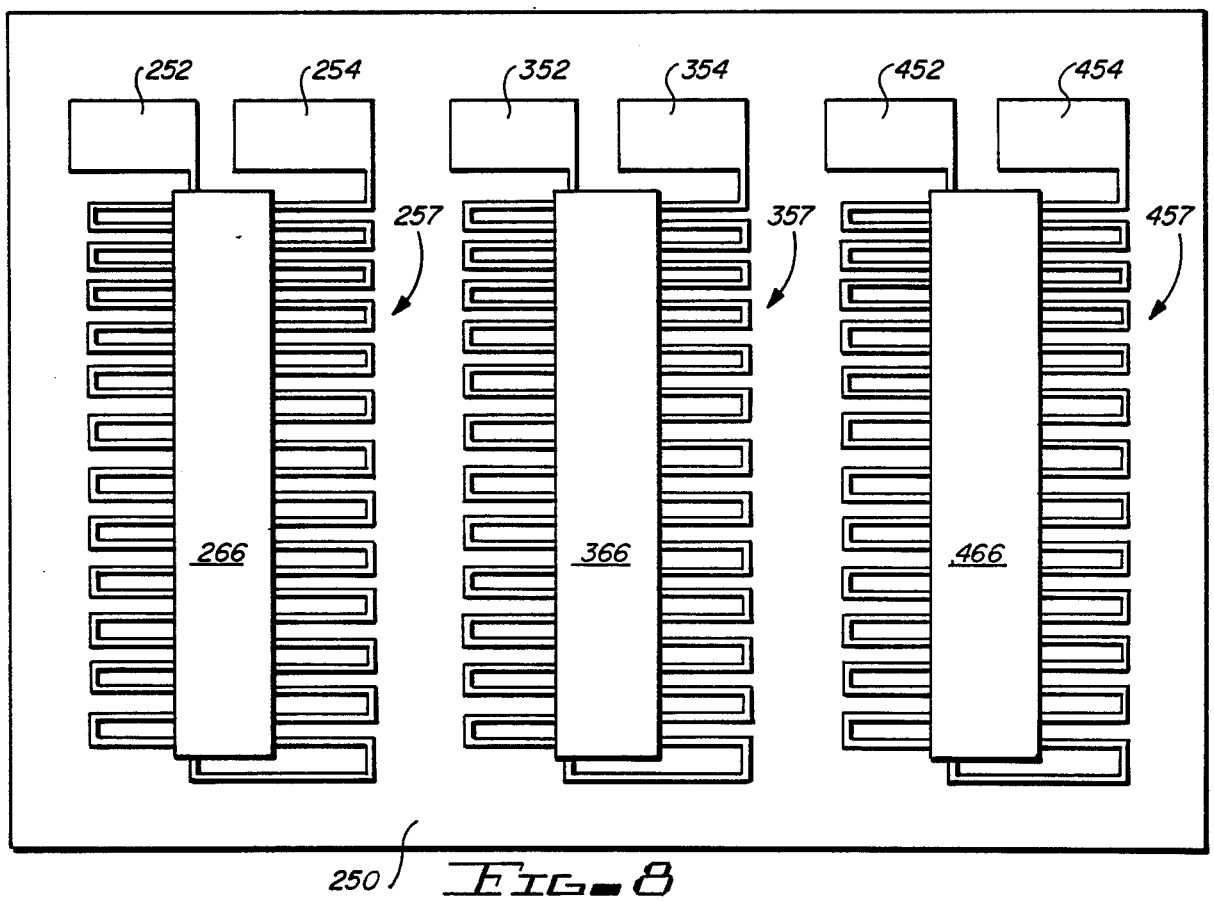
Fig-8

IMPLANTABLE MICROELECTRONIC BIOCHEMICAL SENSOR INCORPORATING THIN FILM THERMOPILE

BACKGROUND OF THE INVENTION

1. Field of the Invention

The present invention relates generally to biochemical sensors used to measure the concentration of a specific chemical dissolved within a fluid, and more particularly, to a biochemical sensor formed by thin film microelectronic fabrication techniques in order to provide a thermopile used to generate a voltage signal representative of the concentration of a chemical dissolved within a fluid.

2. Description of the Prior Art

There has been a well recognized need in the medical field for a sensor capable of being implanted in a human body for providing a continuous indication of the concentration of glucose in the bloodstream. Implantable drug dispensers have been developed to dispense insulin into the bloodstream of persons having diabetes in order to simulate the manner in which the pancreas functions in a non-diabetic. Widespread application of such insulin dispensing devices has largely been frustrated due to the unavailability of an implantable sensor capable of monitoring glucose levels for controlling the rate at which the insulin is dispensed into the bloodstream. Publications stressing the need for the development of such an implantable glucose sensor include Albisser and Spencer, "Electronics and the Diabetic," *IEEE Transactions on Biomedical Engineering*, Vol. BME-29, No. 4, April 1982; *Wall Street Journal*, "Medtronic Researchers Try Hard to Develop In-Body Drug Device", Apr. 12, 1983 and *Diabetes Care*, Vol. 5, No. 3, May–June 1982, "Symposium on Potentially Implantable Glucose Sensors". While the need for an implantable sensor of the type capable of measuring glucose levels has perhaps received the most attention, there are many other drugs besides insulin which might be beneficially dispensed with an automatic dispenser and which require sensors responsive to chemicals other than glucose in order to control the rate at which such drugs are dispensed. There is also a need to continuously measure the concentration of many chemicals in the body independent of their control.

Various types of enzyme probes are known in the art for the purpose of measuring the concentration of glucose or other chemicals dissolved within a solution. For example, Guilbault has recently reviewed a large number of articles describing this type of probe; see Guilbault, G. C., "Future of Biomembrane Probes," *Theory, Design and Biomedical Applications of Solid State Chemical Sensors*, pp. 193–204, CRC Press, 1978. Enzyme probes of this type have been used to measure glucose. In "Problems in Adapting a Glucose-Oxidase Electrochemical Sensor into an Implantable Glucose-Sensing Device," *Diabetes Care*, Vol. 5, No. 3, May–June 1982, the author describes a type of glucose electrode wherein the enzyme glucose oxidase is immobilized upon a polarographic electrode in order to chemically react glucose which contacts the electrode. A polarographic electrode is typically made from a noble metal wire and is biased with an electrical voltage for causing an electrochemical reduction reaction. The enzyme glucose oxidase facilitates the oxidation of glucose into gluconic acid and hydrogen peroxide and consumes oxygen in the process. The disappearance of oxygen, or the appearance of hydrogen peroxide, is measured using a standard polarographic electrode and is proportional to the amount of glucose consumed. Such a glucose electrode has not been successfully implanted for long periods because polarographic measurements are very unstable.

An alternate method of measuring glucose concentrations is to measure the heat evolved by the glucose oxidase enzymatic reaction, as described in U.S. Pat. No. 3,878,049, issued to Tannenbaum, et al. This patent discloses a biochemical temperature sensing analyzer including an uncoated reference thermistor and a second thermistor coated with an enzyme, such as glucose oxidase. The patent specification states that the temperature sensing elements may be thermistors, thermocouples, or pyroelectric devices for generating an electrical signal proportional to the difference in temperature between the enzyme-coated and non-enzyme coated temperature sensing elements. However, the disclosed apparatus includes a mechanism for continuously stirring the reactant-containing liquid, as well as a constant temperature bath into which a container housing the reactant-containing liquid is immersed. Although Tannenbaum refers to this device as a thermal enzyme probe, it is not a "probe" in the classical sense, but rather a benchtop chemical analyzer. Given such limitations, it is clear that such an apparatus is not suitable for being implanted within a human body.

U.S. Pat. No. 3,972,681, issued to Clack et al., discloses a flow-through type thermal detector including a pair of parallel fluid flow paths; one of these paths includes a reactor column wherein an enzyme is immobilized on the surface of small glass beads packed in the column. Similarly, U.S. Pat. No. 4,021,307, issued to Mosbach, discloses a heat sensor disposed within a flow path wherein an enzyme is immobilized within a packed column of glass beads. For obvious reasons, such flow-through systems do not lend themselves to the production of an implantable thermal enzyme electrode.

The patents mentioned above typically suggest the usage of one or more thermistors with a benchtop apparatus for sensing the temperature change caused by a chemical reaction. The practical application of such apparatus has been hampered because they employ thermistors; since thermistors are resistive devices, temperature sensing is performed by conducting a current therethrough and measuring the voltage thereacross. However, the passage of current through the thermistor dissipates power therein and gives rise to self-heating within the thermistor; such self-heating adds an offset to the temperature differential induced solely by the chemical reaction of the glucose or other dissoved chemical. Further, any fluid flow or movement of the thermistor within the fluid will result in a change of the temperature of the thermistor due to variable amounts of heat dissipation. Moreover, the application of current and/or voltage to such thermistors may be regarded as undesirable, particularly for a sensor which is to be implanted within a human body; excitation voltages establish electric fields which are believed to attract proteins and which may activate blood clotting. Finally, thermistors are difficult to match and are subject to drifting whereby two thermistors which may be matched to one another at a given ambient temperature nonetheless become mismatched at a different ambient temperature, thus giving rise to the need for constant temperature baths and/or preheating mechanisms within the abovementioned prior art sensors. Some of these problems have been discussed in a recent paper by Fulton, Cooney and Weaver, "Thermal Enzyme Probe with Differential Temperature Measurements in a Laminar Flow-Through Cell", *Analytical Chemistry*, Vol. 52, No. 3, March 1980, pp. 505-508.

Yet another problem which has been encountered with prior art thermal enzyme probes of the type which employ both enzyme coated and non-enzyme coated probes is that, even in a well stirred solution, thermal eddies exist which can give rise to an apparent temperature differential between the enzyme-coated and non-enzyme coated probes irrespective of the concentration of the chemical under test. Such thermal eddies may thereby give rise to false indications of concentrations of the chemical under test, or alternatively, may tend to offset temperature differentials which would otherwise be present due to the chemical reaction of the chemical under test.

It has also been suggested that thin film thermopiles may be used to measure temperature differentials for certain biomedical applications. In Wunderman and Muray, *Temperature, Its Measurement and Control in Science and Industry*, Vol. 4, Part 3, page 2151, published by The Instrument Society of America, Pittsburgh, Pa. 1972, the construction and application of thin film thermopiles is described for directly measuring temperature differentials on the skin of a segment of the body and for use as detectors in microcalorimetry. Thin film thermopiles are also discussed in G. R. Lahiji, *A Monolithic Thermopile Detector Fabricated Using Integrated Circuit Technology*, Ph.D. Dissertation, Department of Electrical and Computer Engineering, Stanford University, June 1981. However, neither of the aforementioned papers discloses or suggests the use of such a thin film thermopile in conjunction with an immobilized substance, such as an enzyme or other catalyst coating, for the purpose of sensing the concentration of a chemical within a solution.

Accordingly, it is an object of the present invention to provide a chemical transducer for biomedical applications and capable of being implanted within the human body for sensing chemical concentrations in body fluids.

It is another object of the present invention to provide such a chemical transducer adapted to detect concentrations of glucose in the bloodstream by measuring the heat of reaction associated with the enzymatic chemical decomposition of glucose using glucose-specific enzymes.

It is another object of the present invention to provide such a chemical transducer wherein living plant or bacteria cells, or parts thereof, are used to metabolize a chemical under test, and wherein the transducer measures the heat of metabolism associated therewith.

It is still another object of the present invention to provide such a chemical transducer which is highly sensitive while being relatively compact and disposable.

It is yet another object of the present invention to provide such a chemical transducer which is relatively convenient and inexpensive to manufacture and which may be fabricated using conventional integrated circuit thin-film metal deposition and microlithography techniques.

A further object of the present invention is to provide such a chemical transducer or sensor which avoids the requirements for the application of excitation voltages and/or currents in order to obtain a measurement of the concentration of the chemical under test, and which thereby avoids self-heating within the sensor.

A still further object of the present invention is to provide such a sensor capable of sensing a temperature differential within a solution under test and exhibiting high common mode rejection with respect to background ambient temperatures of the solution, thereby avoiding drifting/mismatch problems encountered with differential thermistor sensing, and avoiding the need for constant temperature water baths.

Another object of the present invention is to provide such a sensor adapted to differentially sense temperature between two physical points within the fluid under test and wherein the distance between such two physical points is kept to a minimum to negate the effects of thermal eddies within the fluid under test.

Still another object of the present invention is to provide such a sensor which may be used as an inexpensive and disposable in-vitro clinical analyzer for measuring concentrations of a chemical dissolved in a fluid within a clinical laboratory while avoiding the need for controlled water baths, pre-heating mechanisms, and/or specialized flow paths for the solution under test.

These and other objects of the present invention will become more apparent to those skilled in the art as the description thereof proceeds.

SUMMARY OF THE INVENTION

Briefly described, and in accordance with one embodiment thereof, the present invention relates to an apparatus and a method for determining the concentration of a chemical, such as glucose, dissolved within a fluid, such as human blood, wherein at least one pair, and preferably a plurality of pairs of microelectronic devices are formed upon a supporting substrate using photolithographic techniques. The microelectronic devices may be, for example, thermocouple junctions interconnected to form a thin film thermopile producing a voltage having a temperature dependent magnitude. The thin film thermopile is formed upon a supporting substrate using conventional integrated circuit, thin film metal deposition techniques. The thermopile includes a number of pairs of thermocouple junctions coupled in series connection with one another, each such pair including a reference junction and a sensing junction coupled in series connection with and spaced apart from one another. The thermopile is electrically insulated from fluids into which it is to be immersed by a thin passivation layer formed upon the substrate. A relatively thin film of an immobilized reaction-inducing substance, such as an enzyme or other catalyst, microorganism, or organelle, is then applied proximate to the sensing junctions for initiating a chemical or metabolic reaction of the particular chemical within the fluid for which the concentration is to be determined.

The above-mentioned reaction-inducing substance is either not disposed proximate to the reference junctions or is rendered inactive proximate thereto so that the aforementioned reaction is not initiated in the vicinity of the reference junctions. The heat of reaction, or heat of metabolism, resulting from the reaction initiated in the vicinity of the sensing junctions creates a temperature differential as between the sensing junctions and the reference junctions which induces a differential voltage thereacross. Appropriate lead wires are connected to the terminals of the thermopile for providing the voltage difference signal to an amplifier and measuring circuit for measuring the magnitude of the differential voltage and thereby providing an indication of the concentration of the chemical under test. Such lead wires may merely be thin film metal traces if the amplifier is fabricated within the supporting substrate.

The thermopile is preferably formed by applying two dissimilar materials as thin films to the supporting substrate to form alternating and overlapping series-connected traces. The two dissimilar materials may be first and second metals wherein a first metal, such as antimony, is applied to the substrate using thin film deposition techniques, and a second metal, such as bismuth, is subsequently applied to the substrate again using thin film deposition techniques, the end portions of alternating metal traces being overlapped with one another to form thermocouple junctions. The plurality of sensing junctions are preferably disposed as a grouping upon the substrate to facilitate the coverage thereof by the reaction-inducing substance.

In a preferred embodiment of the present invention used to detect the presence of glucose within a solution, the enzyme glucose oxidase is immobilized over the sensing junctions of the thermopile for causing the chemical decomposition of glucose into gluconic acid and hydrogen peroxide, resulting in the liberation of heat. The immobilized enzyme coating may also incorporate the enzyme catalase for causing the further chemical decomposition of hydrogen peroxide into water and oxygen gas, resulting in the liberation of additional amounts of heat.

The distance by which the sensing junctions and reference junctions are spaced apart from one another is preferably as small as possible in order to minimize the effects of thermal eddies within the solution. To further minimize the effects of such thermal eddies, half of the reference junctions are preferably disposed on each of opposing sides of the grouping of sensing junctions for insuring that the average ambient temperature to which the reference junctions are exposed approximates the ambient temperature to which the sensing junctions are exposed.

The present invention further contemplates the implantation of the sensor described above within the body of a human to measure the concentration of particular chemicals within body fluids, such as the concentration of glucose within the bloodstream.

BRIEF DESCRIPTION OF THE DRAWINGS

FIG. 3 is a graph which depicts the differential output voltage provided by a prototype sensor of the type illustrated in FIG. 1C at various levels of glucose concentration within a solution into which the sensor was immersed.

FIG. 4 is a graph which plots theoretically predicted thermocouple junction temperature differentials versus the concentration of glucose within a test solution, both in the presence or absence of co-immobilized catalase, and both using air or pure oxygen ambient within the solution.

FIG. 6 is an enlarged view of the portion of the sensor shown in FIG. 5 within the dashed circle 6.

FIG. 7A is a cross-sectional view of an alternate embodiment of the microelectronic biochemical sensor wherein the supporting substrate is made relatively thin below those areas upon which the thermocouple junctions are formed, and wherein the reaction-inducing substance is applied to the substrate on a side opposite to that upon which the thermocouple junctions are formed.

FIG. 7B is a view of the sensor shown in FIG. 7A taken through lines 7B–7B.

FIG. 8 illustrates a substrate upon which a multiple number of biochemical sensors have been formed.

FIG. 9 illustrates, in cross-section, a catheter having a hollow piercing tip in which is secured a microelectronic biochemical sensor of the type shown in FIG. 5.

DETAILED DESCRIPTION OF THE PREFERRED EMBODIMENT

Figure 1A:
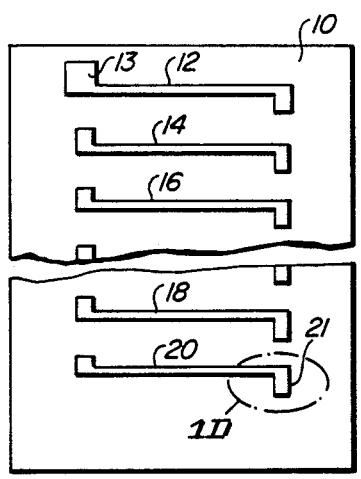
FIGS. 1A-1C are top views of a substrate upon which a sensor of the aforementioned type is formed in a step-by-step manner.

FIGS. 1A-1E illustrates a prototype chemical transducer or microelectronic biochemical sensor which was constructed according to the teachings of the present invention. Within FIG. 1A, reference numeral 10 designates a supporting substrate which, in the case of the prototype device, is an ordinary glass microscope slide. Preferably, the supporting substrate 10 is a single, continuous piece of material such as glass, silicon, ceramic, or plastic. The use of silicon as the substrate offers the advantage of allowing electronic components other than the sensor to be fabricated within the substrate, such as an integrated circuit pre-amplifier to amplify the electrical signal provided by the sensor.

A plurality of metal traces, such as those designated by reference numerals 12-20 of a first type of metal, such as bismuth, are formed upon support substrate 10. Metal traces 12-20 are formed by first depositing a thin film of the first type of metal upon substrate 10 using conventional thin film metal deposition techniques which have been developed in the semiconductor integrated circuit industry. Such thin film deposition techniques are well-known in the art; further details concerning such thin film deposition techniques may be found in *Polycrystalline and Amorphous Thin Films and Devices* by L. L. Kazmerski, Academic Press, New York, 1980; *Thin and Thick Films for Hybrid Micro-electronics*, by Z. H. Meiksin, Lexington Books, Lexington, Mass., 1976; *Thin Films* by Weaver et al., Wykeham Publications, New York, 1971; and *Handbook of Thin Film Technology*, by Maissel et al., McGraw Hill, New York, 1970, which publications are hereby incorporated by reference.

Figure 1B:
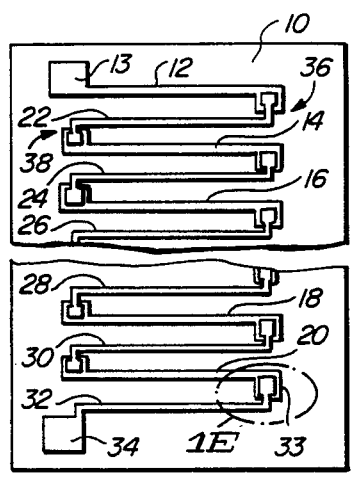

As shown in FIG. 1A, metal trace 12 includes an enlarged portion at the left most end thereof serving as a first terminal or pad 13 for attachment of a lead wire thereto. The right most end of metal trace 12 is enlarged to a somewhat lesser extent than the left most end to facilitate the formation of a thermocouple junction 36 in a manner to be described below with reference to FIG. 1B. Metal traces 14-20 include enlarged portions at their left most and right most ends to facilitate the formation of thermocouple junctions in a manner to be described below. For example, the right most end 21 of metal trace 20 is shown in FIG. 1D. The configuration of metal traces 12-20 is determined by patterning and etching the thin film of the first type of metal deposited upon the surface of substrate 10 using conventional microlithographic techniques commonly used within the semiconductor industry.

After the metal traces 12-20 are patterned upon the surface of substrate 10, a second type of metal, such as antimony, is deposited as a thin film upon the surface of substrate 10 using the thin film metal deposition techniques previously described. The thin film of the second metal is similarly patterned and etched to form a plurality of metal traces designated within FIG. 1B by reference numerals 22-32. As shown in FIG. 1B, metal traces 22-32 extend generally parallel to and are interleaved with metal traces 12-20. The end portions of metal traces 22-30 are slightly enlarged and lie above and within the enlarged end portions of metal traces 12-20. Metal trace 32 includes a right most end 33 which overlies the right most end 21 of metal trace 20, as shown within FIG. 1E. The left most end of metal trace 32 is enlarged and serves as a second terminal or pad 34 for attachment of a second lead wire to the sensor.

Figure 2:
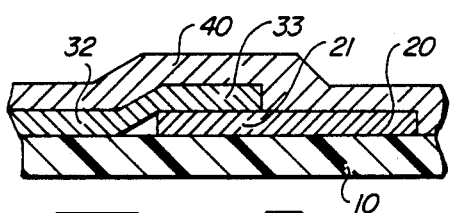
FIG. 2 is a cross-sectional view of one of the sensing junctions taken through lines 2—2 as indicated within FIG. 1C.

Each point at which the ends of two dissimilar metal traces contact one another creates one of a series-connected pair of thermocouple junctions; each such pair of thermocouple junctions gives rise to a minute electrical potential which is proportional in magnitude to the temperature difference between the pair of thermocouple junctions. FIG. 2 illustrates in cross-section the thermocouple junction formed between the right most end 33 of metal trace 32 and the right most end 21 of metal trace 20.

As shown in FIG. 1B, the various thermocouple junctions are interconnected in series between terminal 13 and terminal 34. The plurality of thermocouple junctions may be grouped in pairs, each pair consisting of one thermocouple junction formed upon the right most side of substrate 10 and a second thermocouple junction directly connected thereto on the left most side of substrate 10. For example, the thermocouple junctions designated by reference numerals 36 and 38 comprise one such pair. As shown in FIG. 1B, such pairs of thermocouple junctions are in turn coupled in series connection with one another between terminals 13 and 34. One such thermocouple junction may actually be formed via a lead wire bonded to one of the pads forming terminals 13 and 34.

Within the prototype sensor device shown in FIGS. 1A-1E, 27 pairs of such thermocouple junctions are provided. The right most thermocouple junction of each such pair may be regarded as a sensing junction, while the left most thermocouple junction of each such pair may be regarded as a reference junction, as will be more clearly understood from the description of FIG. 1C below. As shown in FIG. 1B, the reference junctions and sensing junctions are spaced apart from one another. Within the prototype sensor which was constructed, the distance by which such sensing and reference junctions were spaced apart was approximately 0.25 inch, although this distance may advantageously be made smaller to minimize the effects of thermal eddies upon the sensor, as is described more fully below. The plurality of thermocouple junctions thus formed may be referred to as a thermopile.

The differential electrical potential created by the sensing and reference junctions within each pair of thermocouple junctions is zero when such junctions are at equal temperatures. In order to utilize the sensor shown in FIG. 1B as a chemical transducer, a differential temperature is created between the sensing and reference junctions for causing a corresponding differential electrical potential to be provided across terminals 13 and 34. Such a differential temperature may be created by localizing chemical or metabolic reactions which are either endothermic or exothermic in the vicinity of the sensing junctions wherein the heat of reaction (or heat of metabolism) associated with such chemical reactions (or metabolic reactions) either decreases or increases the temperature of the sensing junctions relative to the temperature of the reference junctions. Such localized chemical reactions may be induced by applying a thin layer of a catalyst, such as an enzyme, above and/or proximate to the sensing junctions for initiating a particular chemical reaction in the vicinity thereof involving the chemical for which the concentration is to be determined. Alternatively, locallized metabolic reactions may be induced in proximity to the sensing junctions, as is described in greater detail below.

In order to produce a sensor of the type described above, the thermopile device shown in FIG. 1B is first passivated, i.e., physically and electrically insulated from the solution into which the sensor is to be immersed. One such method of passivating the thermopile is to first coat the device shown in FIG. 1B with a thin film of photoresist (a light sensitive polymer membrane commonly used in the semiconductor industry for practicing photolithography) and subsequently depositing a thin film of silicon nitride thereabove. Other standard passivation techniques may also be used. Holes may be opened within the passivation layer above pads 13 and 34 to allow for the attachment of lead wires thereto.

Figure 1C:
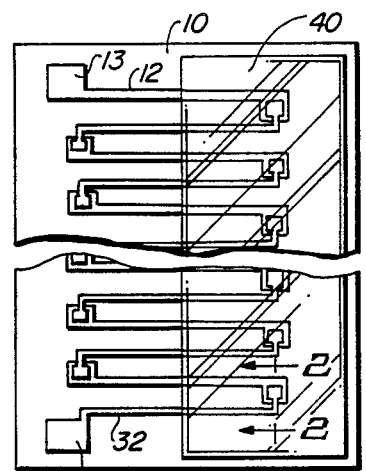
Figure 1D:
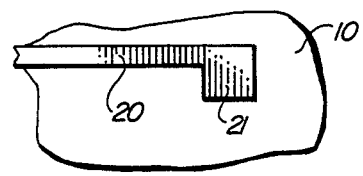
FIGS. 1D and 1E are enlarged views of the circled portions designated 1D and 1E within FIGS. 1A and 1B, respectively.
Figure 1E:
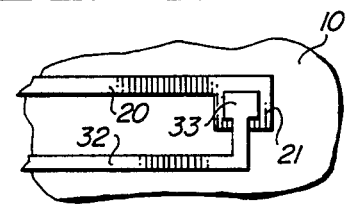

Following application of the passivation layer as described above, a thin film of a catalyst or enzyme, designated by reference numeral 40 within FIG. 1C, is applied to substrate 10 overlying the sensing junctions but not overlying the reference junctions. With respect to the prototype device illustrated in FIGS. 1A-1E, enzyme coating 40 consists of an immobilized layer of the enzyme glucose oxidase.

In operation, the prototype device shown in FIGS. 1A-1E is immersed in a solution containing dissolved glucose. As is known to those skilled in the art, glucose oxidase triggers the chemical decomposition of glucose into gluconic acid and hydrogen peroxide and liberates heat in the process. Some of the liberated heat is conducted through the immobilized enzyme layer and passivation layer to the sensing junctions, and some of the liberated heat is lost to the solution in which the sensor is immersed. The heat conducted to the sensing junctions increases the temperature thereof relative to the temperature of the reference junctions, thereby creating a temperature differential. The temperature differential causes each pair of sensing and reference junctions to create a differential voltage proportional to the amount of heat liberated by the chemical reaction. Since the pairs of thermocouple junctions are connected in series, the differential voltage established by each pair of thermocouple junctions is multiplied by the number N of such junction pairs. This multiplied differential voltage is provided across terminals 13 and 34 and may be conducted by lead wires attached thereto (not shown) to an amplification circuit for amplifying and measuring the differential voltage.

Methods for immobilizing glucose oxidase and other enzymes upon substrate 10 are well-known in the art. Publications disclosing further details regarding such enzyme immobilization methods include *Immobilized Enzymes in Analytical and Clinical Chemistry*, by Carr and Bowers, Wiley Interscience, New York, 1980, pages 197-310; *Analysis and Control of Immobilized Enzyme Systems*, by Thomas and Kernevez, Amsterdam, North Holland, 1976; and *Enzyme Engineering*, by Brown et al., Plenum, New York, 1978, Vol. 4, which publications are hereby incorporated by reference.

FIG. 3 is a graph which shows the results of the prototype glucose sensor shown in FIG. 1C when immersed in a glucose solution. The vertical axis of the graph indicates the thermopile voltage output (in microvolts) as a function of the glucose concentration (in milliMoles) in the solution in which the thermopile is immersed. The glucose solutions in which the prototype sensor was immersed were aqueous solutions saturated with 100 percent oxygen, and no catalase was immobilized over the sensing junctions. The measured data points drawn in the graph of FIG. 3 indicate that the response of the thermopile sensor is approximately linear, as approximated by the straight line drawn between the measured data points. Theoretically, the straight line should pass through the zero point of the graph, since the absence of any glucose within the solution should not give rise to a differential output voltage. The scatter of the measured data points within the graph of FIG. 3 is most likely due to errors due to thermal fluctuations within the solution or electrochemical offsets generated by the breakdown of the insulating photoresist layer applied to the prototype device.

Theoretical calculations have been performed in an effort to predict the range of glucose concentration levels over which the prototype sensor shown in FIG. 1C will provide a linear response under various test conditions. With reference to FIG. 4, a graph is shown wherein the vertical axis indicates the theoretical temperature differential which should be observed, and the horizontal axis indicates glucose concentration in units of milliMoles per liter. The lowermost curve designated by reference numeral 42 represents the theoretical temperature differential which would be observed by the prototype sensor when the glucose solution is saturated with air and when no catalase is immobilized within the enzyme coating 40 (see FIG. 1C). The second curve within FIG. 4 designated by reference numeral 44 represents the temperature differential which would be observed by the prototype sensor device when the glucose solution is saturated with pure oxygen, but with no catalase incorporated within enzyme coating 40. The third curve within FIG. 4 designated by reference numeral 46 depicts the theoretical temperature differential to which the prototype sensor would be exposed if the glucose solution were saturated with air and if catalase were immobilized along with the glucose oxidase within enzyme coating 40. Finally, the fourth curve within FIG. 4 designated by reference numeral 48 indicates the temperature differential which the prototype sensor would yield if the glucose solution were saturated with pure oxygen and if catalase were incorporated within enzyme coating 40 along with the immobilized glucose oxidase.

Curve 44 within FIG. 4 should correspond with the operating conditions under which measurements were actually taken with the prototype sensor as reflected within FIG. 3. Given the data points shown within FIG. 3, one may compute the corresponding temperature differentials observed by the prototype sensor device by assuming that each thermocouple junction pair produces an electric potential of 110 microvolts per degree Centigrade of temperature differential. Since the prototype device includes 27 thermocouple junction pairs, its sensitivity was thus assumed to be 2,970 microvolts per degree Centigrade. Application of the foregoing to the measured output voltage data points shown in FIG. 3 resulted in computed temperature differentials for the prototype sensor within the same order of magnitude as those predicted by curve 44 within FIG. 4. The glucose oxidase applied to the prototype device may very well have been contaminated with catalase; accordingly, the measurements plotted in FIG. 3 may actually bear a closer match to the theoretical curve 48 (pure oxygen and catalase present) in FIG. 4.

While the foregoing description of the prototype device relates to the use of an enzyme coating to initiate chemical reactions in order to create a temperature differential between the sensing and reference junctions, other substances besides enzymes may be used to create such a temperature differential. For example, microorganisms such as yeast or bacteria may be immobilized in a gel and thereby applied proximate to the sensing junctions in order to metabolize the chemical under test. The heat of metabolism creates a temperature differential which may be detected by the sensing and reference junctions of the microelectronic biochemical sensor in order to provide an indication of the concentration of the chemical under test within the solution.

Strains of yeast cells are known which metabolize glucose. In fact, some strains of yeast cells are known which metabolize only glucose and not other substances, thus enabling a sensor using such yeast cells to be highly selective. Such strains of yeast are disclosed in "The Yeasts" edited by Jacomina Lodder, published by North-Holland Publishers, Amsterdam, 1970. Because the yeast cells stay alive even after being immobilized upon the sensor, the yeast cells are self-renewing, thereby allowing the sensor to have an extended lifetime. Furthermore, the heat of metabolism associated with the reduction of glucose by yeast may be greater than the corresponding heat of reaction associated with the chemical reduction of glucose by enzymes because yeast is capable of decomposing glucose completely to ethanol.

Methods for immobilizing yeast in a solid gel are well known. One recent paper describing such methods is Kuu and Polack, "Improving Immobilized Biocatalysts by Gel Phase Polymerization", *Biotechnology and Bioengineering*, Vol. XXV, pp. 1995-2006, 1983.

Similarly, strains of bacteria are known which metabolize glucose or other chemicals, the concentrations of which are of interest. See, for example, "The Genus Aspergillus" authored by Kenneth B. Raper et al., published by Williams & Wilkins Publishing, Baltimore, Md., 1965. Furthermore, organelles, i.e., mitochondria (portions of living cells), are known which are capable of metabolizing glucose and other chemicals of interest. Techniques for isolating such organelles from living cells are known to those skilled in the art, as exemplified within "Biomembranes Part A and B", *Methods in Enzymology*, Vols. 31 and 32, Academic Press, New York, N.Y. Such bacteria and organelles can be immobilized upon a sensor of the type described herein by the methods taught in the above-mentioned paper by Kuu and Polack.

Figure 5:
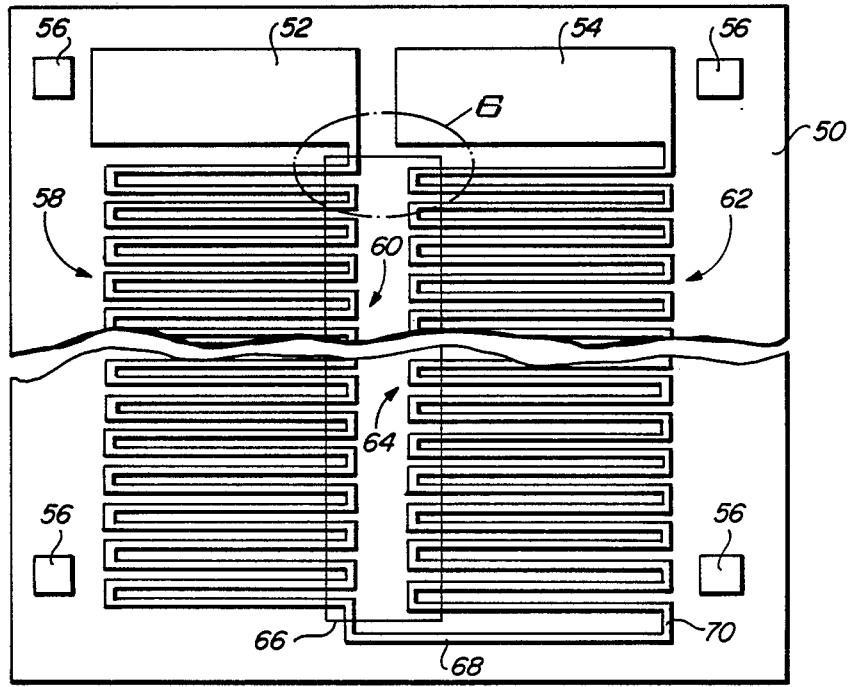
FIG. 5 illustrates a preferred embodiment of a sensor constructed according to the teachings of the present invention and wherein half of the reference junctions are disposed on each side of a central grouping of sensing junctions.

FIG. 5 discloses one preferred embodiment of the present invention wherein the sensor is fabricated upon a silicon substrate 50. Bonding pads 52 and 54 are provided for attachment of lead wires to the sensor device. The square shaped indicia designated by reference numerals 56 within the four corners of substrate 50 are merely alignment markings so that the photolithographic masks used to pattern the metal traces and enzyme coating are properly aligned with one another. The sensor device shown in FIG. 5 includes a first set of seventy-five reference junctions designated by reference numeral 58 which are alternately interconnected with a first set of seventy-five sensing junctions designated by reference numeral 60. A second set of seventy-five reference junctions is formed along the right most side of substrate 50 and are designated by reference numeral 62; reference junctions 62 are similarly alternately interconnected with a second set of seventy-five sensing junctions designated by reference numeral 64.

The first set 60 and second set 64 of sensing junctions are covered by an immobilized reaction-inducing substance such as an enzyme coating designated by reference numeral 66 within FIG. 5. As shown in the lowermost portion of FIG. 5, the lowermost sensing junction within first group 60 is connected in series by metal trace 68 to the lowermost reference junction 70 within second set 62 of reference junctions. In this manner, all 150 pairs of sensing and reference junctions formed upon substrate 50 are coupled in series between pads 52 and 54.

Referring briefly to FIG. 6, it will be noted that the manner in which the reference and sensing thermocouple junctions of FIG. 5 are formed is essentially identical to the process described with regard to the prototype device shown in FIG. 1C. Pad 52 is coupled by a metal trace 72 to a somewhat enlarged thin film antimony portion 74 which overlies the enlarged left most end 76 of a bismuth metal trace 78 in order to form the uppermost reference junction 80 within the first group of reference junctions 58. Similarly, the right most end of antimony trace 82 overlies the right most end of bismuth trace 78 to form the uppermost sensing junction 84 within the first group of sensing junctions 60.

The first group of reference junctions 58 are spaced apart from the first group of sensing junctions 60 by a distance of approximately 0.90 millimeters in the preferred embodiment of the present invention. The interconnecting metal traces are each preferably 6 micrometers wide and 1 micrometer thick, while the spacing between adjacent metal traces is 5 micrometers. The entire array of sensing and reference junctions shown in FIG. 5 requires an area measuring only approximately 1.85 millimeters square. The above-described dimensions for the metal traces shown in FIG. 5 are well within the capabilities of thin film deposition and photolithographic processing technologies.

As shown in FIG. 5, the first set of sensing junctions 60 and the second set of sensing junctions 64 are grouped together upon substrate 50 in order to facilitate the coverage thereof by enzyme coating 66. As is also apparent from FIG. 5, half of the reference junctions (first set 58) are located to the left of the grouping of sensing junction 60 and 64, while the other half of the reference junctions (second set 62) are located to the right of the grouping of the sensing junctions. This arrangement of reference junctions further contributes to the minimization of measurement errors due to the existence of thermal eddies with the solution. In the event that the ambient temperature of the solution differs between the first set 58 and second set 62 of reference junctions, the average temperature to which the reference junctions are exposed will closely approximate the ambient temperature of the solution in the vicinity of the sensing junctions 60 and 64.

The thin film thermopile shown in FIG. 5 must be protected before it is immersed in a conducting solution or implanted in a human body in order to prevent the metal traces within the thermopile from being shorted together. As mentioned above with regard to the prototype sensor shown in FIG. 1C, one such method for protecting the thermopile is to passivate the sensor in order to electrically insulate the thin film thermopile from the fluid surrounding the sensor. Among those materials which may be used to passivate and insulate the thin film thermopile formed upon silicon substrate 50 are various types of photoresist, thin films of deposited silicon nitride, polyimide, parylene, glow discharge polymers, sputtered ceramic coatings, and combinations of the foregoing types of films in multiple layers. Initial tests indicate that photoresist films successfully insulate the thin film thermopile for rather short periods of time. Preferably, parylene or polyimide is used to form the passivating membrane. The presence of such a passivating film between the thermocouple sensing junctions and the immobilized enzyme matrix does not significantly decrease the sensitivity of the sensor even if the passivating film is several microns thick.

Lead wires are preferably connected to output terminal pads 52 and 54 prior to the application of the passivation layer. If such lead wires are coupled to amplification circuitry external from the supporting substrate 50, then an epoxy coating is applied to such lead wires for electrical insulation. RF sputtering of a passivating agent, such as silicon nitride, may then be performed to passivate the thin film thermopile. In order to increase the water resistance of the sensor and to protect the relatively high impedance of the thermopile from the slow degrading effects of hydration which occur with most polymer coatings, multiple layers of thin film ceramic material such as $Ta_2O_5$ and $ZrO_2$ may be incorporated within the passivation layer.

As an alternative to bonding the lead wires to pads 52 and 54 before application of the passivation layers, the bonding of the lead wires may be deferred until after the application of the passivation layers and immobilized enzyme layer. In this event, the pads 52 and 54 are either masked so as to prevent the application of the passivation layer thereover, or the passivating membrane is later etched away from the area overlying pads 52 and 54. Lead wires are then bonded to pads 52 and 54, and an insulating and sealing material such as epoxy, silicon rubber, or additional parylene is deposited in the vicinity of the pads and around the lead wires to insulate the same from the solution.

With reference to FIG. 5, enzyme coating 66 is preferably immobilized over the entire surface of substrate 50. Immobilization of the enzyme may be achieved by either covalent bonding or entrapment methods. If covalent bonding is used, then the enzyme is covalently bonded to either the passivating membrane or a second membrane (the enzyme support matrix) deposited above the passivating membrane. On the other hand, if the entrapment method is used, the enzyme is entrapped within a polymer membrane, e.g., polyacrylamide or polyvinyl chloride, applied as a thin film above the passivating membrane. In either case, a photographic mask having a blackened area corresponding in shape and size to enzyme coating 66 shown in FIG. 5 is applied over the upper surface of substrate 50, and substrate 50 is subsequently exposed through the aforementioned mask to infrared light. The infrared radiation denatures the enzyme immobilized upon the surface of substrate 50, with the exception of the area blocked by the darkened area of the aforementioned mask. Those portions of the immobilized enzyme denatured by the exposure to the infrared radiation lose their activity and are incapable of initiating the chemical reaction within the solution under test.

An alternative method of applying the enzyme coating is to dissolve an excess of the particular enzyme in a polymeric carrier such as polyacrylamide, polyvinyl chloride, or silicone rubber and to apply the resulting material as a thin film over the sensing junctions of the thermopile using a hypodermic syringe.

Other methods of applying the reaction-inducing substance to the sensor may also be used. For example, the polymer containing the reaction-inducing substance may be applied to the substrate using the same silk screening techniques as are commonly used in the fabrication of hybrid electronic circuits. Yet another method of applying the reaction-inducing substance to the sensor employs carboiimide coupling. In practicing this method, the substrate 50 is masked with a metal mask, and carbon is vacuum evaporated onto the substrate through the mask. The mask prevents the vacuum evaporation of carbon over areas adjacent the reference junctions. The mask is then removed, and the reaction-inducing substance, such as the enzyme glucose oxidase, is carboiimide coupled to the masked carbon film, whereas the glucose oxidase does not bond with the substrate in those areas where the carbon film is absent. A reference which describes this method of covalently coupling to a thin layer carbon support is J. A. Osborn et al., "Use of Chemically Modified Activated Carbon as a Support for Immobilized Enzymes," *Biotechnology and Bioengineering*, Vol. XXIV, pp. 1653–1669, 1982.

Following fabrication of the thermopile sensor shown in FIG. 5 in the manner described above, substrate 50 is preferably mounted in a ceramic package, and a final coat of water resistant polymer, such as polyimide, is applied around the periphery of the device, particularly around the bonding pads and output lead wires. Care is taken to avoid application of the final coat of water resistant polymer over the immobilized enzyme layer.

FIGS. 7A and 7B illustrate an alternate embodiment of the present invention wherein the reaction-inducing substance is applied to the surface of the substrate opposite the surface upon which the thermopile is applied. With reference to FIG. 7A, supporting substrate 150, which may be a portion of a silicon wafer, includes an upper surface and opposing lower surface designated by reference numerals 151 and 153, respectively. The central portion of lower surface 153 is micromachined to form a relatively thin portion 155 of substrate 150. Methods for micromachining silicon wafers are well known in the art; further details of such methods may be found in Angel et al., "Silicon Micromechanical Devices," *Scientific American,* March, 1983, pp. 45–55, incorporated herein by reference.

A thermopile 157 is formed upon upper surface 151 using thin-film deposition techniques of the type described above in regard to FIGS. 1A, 1B and 5. The thermopile 157 includes bonding pads 152 and 154 similar to bonding pads 52 and 54 shown within FIG. 5. As shown in FIG. 7B, the plurality of reference and sensing junctions within thermopile 157 are formed upon relatively thin portion 155 of substrate 150.

Following the formation of thermopile 157, a container or housing 159 is attached to the perimeter of supporting substrate 150 to completely seal upper surface 151 and thermopile 157 formed thereupon, thus forming a fluid-impermeable cavity 161 about upper surface 151 of supporting substrate 150.

After encapsulating supporting substrate 150 within housing 159 in the manner described above, a reaction-inducing substance 166, such as an enzyme, is immobilized upon lower surface 153 of supporting substrate 150 over relatively thin portion 155 directly below the sensing junctions of thermopile 157, as shown in FIGS. 7A and 7B. The heat of reaction (or heat of metabolism) resulting from the reactions induced by substance 166 is conducted through relatively thin portion 155 of supporting substrate 150 to the sensing junctions of thermopile 157, thereby inducing a temperature differential between the sensing junctions and reference junctions thereof. Because the supporting substrate 150 is relatively thin in the region wherein the reaction-inducing substance 166 is applied, lateral heat transfer through supporting substrate 150 between the sensing and reference junctions of thermopile 157 is minimized. Furthermore, housing 159 isolates thermopile 157 from the solution in which the sensor is immersed or surrounded; air cavity 161 minimizes heat conduction from the upper surface 151 of supporting substrate 150, thereby allowing the sensing junctions of thermopile 157 to sense a greater temperature differential than might otherwise be possible.

Those skilled in the art will appreciate that multiple sensors may be formed upon the same supporting substrate to simultaneously sense the presence of a plurality of different chemicals within a solution under test. As shown in FIG. 8, three thermopiles 257, 357, and 457 may be formed upon a single supporting substrate 250. Each of thermopiles 257, 357, and 457 is formed in a manner substantially similar to that described above with regard to the sensor illustrated in FIG. 5. Thus, thermopile 257 includes bonding pads 252 and 254 for allowing the interconnection of wires to thermopile 257 for conducting the differential voltage signal developed thereacross. Similarly, thermopile 357 includes bonding pads 352 and 354, and thermopile 457 includes bonding pads 452 and 454.

As in the case of the sensor described with regard to FIG. 5, a reaction-inducing substance 266 is applied proximate to the sensing junctions of thermopile 257 for inducing a chemical or metabolic reaction of a first type in order to sense the presence and concentration of a first chemical. Similarly, second and third reaction-inducing substances 366 and 466 are applied proximate to the sensing junctions of thermopiles 357 and 457 for sensing concentrations of second and third chemicals within the solution under test. Reaction-inducing substances 366 and 466 may either be the same as reaction-inducing substance 266 (for error-checking redundancy) or entirely different substances for allowing the simultaneous sensing of three different chemicals within the solution under test. The methods of passivating substrate 250 to isolate thermopiles 257, 357, and 457 from the solution under test may be the same as those described above with regard to FIG. 5.

Various applications may be made of the sensor device described above. Such a sensor may be used as a laboratory tool in the form of a dip probe for the routine measurement of glucose or other chemicals in a variety of test solutions. Because of the relatively low manufacturing cost and compact size of such sensors, such sensors could be used once and disposed after each use.

Such a sensor is also suitable for implantation in the human body, for example, to measure levels of glucose concentration in the bloodstream in order to regulate the release of insulin from an implanted infusion pump. Sensors of the type described above may also be secured within the tip of a hollow needle or catheter for insertion within body tissue and body cavities, respectively. The manner of securing such a sensor within a hollow needle or catheter, and the manner of routing wires from the sensor to amplication/measuring circuitry may be generally similar to that disclosed in U.S. Pat. No. 4,020,830 issued to Johnson et al., the disclosure of which patent is incorporated herein by reference.

FIG. 9 illustrates one method of introducing the above-described microelectronic biomedical sensor into a human body. As shown in FIG. 9, a hollow needle or catheter 500 is provided, one end 502 of which is bevelled to enable insertion of the needle in body tissue and the like. Disposed in the needle lumen near bevelled end 502 is a microelectronic biomedical sensor 504 constructed as earlier described, for example, with respect to FIG. 5 with a selective catalyst coating such as the enzyme glucose oxidase to catalzyze the chemical reaction of glucose in the bloodstream. Sensor 504 is mounted on a base 506 on which are deposited bonding pads 508 to which conducting wires 510 are coupled. Bonding wires 512 connect the conducting wires 510 to sensor 504. Sensor 504 and associated components are encapsulated in a solution-impervious material 514 having an opening 516 for exposing the sensing and reference junctions of the thin film thermopile formed on sensor 504. The conductors 510 extend proximally in the lumen of needle 500 and in encapsulation material 514 to a point (not shown) where they would exit from the needle for coupling to some type of readout apparatus.

As mentioned above, a sensor of the type described herein may use the enzyme glucose oxidase to catalyze the chemical reaction of glucose. Such a sensor might also utilize the below-listed enzymes and any associated co-factors in order to detect and measure concentrations of the corresponding chemicals listed below:

1. the enzyme hexokinase (and co-factor ATP) for detecting glucose concentrations;
2. the enzyme glucose dehydrogenase (and co-factor NADP) for detecting glucose concentrations;
3. the enzyme cholesterol oxidase to measure concentrations of cholesterol;
4. the enzyme lactase for measuring concentrations of lactose;
5. the enzyme urate oxidase for measuring concentrations of uric acid;
6. the enzyme trypsin to measure concentrations of benzoyl-1-arginine ethyl ester;
7. the enzyme apyrase for measuring the enzymatic hydrolysis of ATP into AMP; and
8. the enzyme penicillinase for measuring concentrations of penicillin.

While the foregoing description refers to the use of the metals antimony and bismuth in order to form a thermopile for use in the biochemical sensor, other materials may be used to form the thermopile. Any two dissimilar materials which, when brought together at a junction, give rise to a thermoelectric potential, may be used. Such dissimilar materials may, for example, be semiconductors, metal alloys, or alloys of the chemical element tellurium. Methods for using such materials to form thermocouple junctions are well known in the art, as exemplified within "Thermoelectricity: Science And Engineering" by Robert R. Heikes et al., Interscience, New York, N.Y., 1961, Chapter 11, pages 339–387, incorporated herein by reference.

While the presently preferred microelectronic devices from which to construct the sensing and reference devices need to detect a differential temperature are series-coupled pairs of thermocouple junctions, those skilled in the art will appreciate that other microelectronic devices which exhibit temperature dependent characteristics may also be used to construct a biochemical sensor of the type herein described. For example, pairs of matched semiconductor diodes may be formed within the same substrate to provide sensing and reference devices for providing a differential voltage proportional to the temperature difference therebetween. When multiple pairs of such diodes are used, the sensing diodes may be coupled in series with one another and the reference diodes may also be coupled in series with one another. The chain of forward-biased, series-coupled sensing diodes are coupled at one end to a common terminal; similarly, the chain of forward-biased, series-coupled reference diodes are coupled at one end to the common terminal. The opposite ends of the chains of sensing and reference diodes are coupled to first and second sensing terminals, respectively. Constant current source circuitry either external to the biochemical sensor or incorporated within the same substrate provides two constant and equal currents through the two chains of diodes. The reaction-inducing substance is applied proximate to the sensing diodes but not proximate to the reference diodes. The differential temperature created between the sensing and reference diodes due to the presence of the chemical under test results in a differential voltage across the first and second sensing terminals proportional to the magnitude of the temperature differential, and hence, proportional to the concentration of the chemical under test.

Those skilled in the art should now appreciate that a sensor capable of providing an electrical indication of the concentration of a chemical present within a fluid has now been described, which sensor may be used as both an inexpensive and disposable in vitro clinical analyzer gas well as an implantable chemical transducer for monitoring concentrations of chemicals, such as glucose, within the human body. The disclosed sensor i highly sensitive while inherently providing high common mode rejection of background fluid temperatures and avoids the need for external excitation voltages and/or currents. The relatively small dimensions of the disclosed sensor contribute toward the minimization of errors which could otherwise be introduced due to the presence of thermal eddies within the solution under test.

While the present invention has been described with regard to a preferred embodiment thereof, it should be understood that the description is for illustrative purposes only and is not to be construed as limiting the scope of the invention. Various modifications and changes may be made by those skilled in the art without departing from the true spirit and scope of the invention as defined by the appended claims.

We claim:

1. A sensor for providing an electrical voltage representative of the concentration of a chemical dissolved in a fluid, said sensor comprising in combination:
    a. a supporting substrate;
    b. a thin film thermopile disposed upon said supporting substrate, said thin film thermopile including a plurality of pairs of thin film thermocouple junctions, each of said pairs of thermocouple junctions including a reference junction and a sensing junction electrically coupled in series connection with one another and spaced apart from one another, said reference junction and said sensing junction within each pair of thin film thermocouple junctions creating a temperature-dependent voltage when said reference junction and said sensing junction are electrically coupled in series connection, said plurality of pairs of thermocouple junctions being electrically coupled in series connection with one another between first and second terminals;
    c. a layer of a substance disposed proximate to each of said sensing junctions, said substance facilitating chemical reactions involving said chemical dissolved in said fluid adjacent said sensing junctions but not adjacent said reference junctions; and
    d. wiring means coupled to said first and second terminals of said plurality of pairs of thin film thermocouple junctions for providing a voltage difference signal proportional to a difference in temperature proximate the sensing and reference junctions arising from chemical reactions facilitated by said substance.

2. A sensor as recited by claim 1 wherein said plurality of pairs of thin film thermocouple junctions are formed by alternating, series-connected traces of first and second materials, respectively, said first material being different from said second material for creating a thermoelectric potential when brought together at a junction.

3. A sensor as recited by claim 2 wherein said first and second materials are each metals.

4. A sensor as recited by claim 3 wherein said first and second materials are Antimony and Bismuth, respectively.

5. A sensor as recited by claim 2 wherein said first and second materials are each semiconductors.

6. A sensor as recited by claim 2 wherein said first and second materials are each metal alloys.

7. A sensor as recited by claim 2 wherein said first and second materials are each alloys of the chemical element Tellurium.

8. A sensor as recited by claim 1 wherein said substance is a catalyst.

9. A sensor as recited by claim 8 wherein said catalyst is an enzyme.

10. A sensor as recited by claim 8 wherein said catalyst includes glucose oxidase for causing the chemical decomposition of glucose into gluconic acid and hydrogen peroxide.

11. A sensor as recited by claim 10 wherein said catalyst includes catalase for causing the chemical decomposition of hydrogen peroxide into water and oxygen gas.

12. A sensor as recited by claim 1 wherein said substance is a microorganism.

13. A sensor as recited by claim 1 wherein said substance is an organelle.

14. A sensor as recited by claim 1 wherein said sensing junctions are disposed upon said substrate as a grouping to facilitate the coverage by said substance of said grouping of sensing junctions, and wherein half of said reference junctions are disposed on one side of said grouping while the other half of said reference junctions are disposed on an opposite side of said grouping for the purpose of cancelling the effects of thermal eddies within said fluid.

15. A sensor as recited by claim 1 further including a layer of insulating material disposed over said plurality of pairs of thin-film thermocouple junctions to electrically insulate said plurality of pairs of said thin film thermocouple junctions from said fluid, said layer of said substance being disposed upon said layer of insulating material.

16. A sensor as recited by claim 1 wherein said supporting substrate includes a relatively thin portion having a first surface on one side thereof upon which said plurality of thin film thermocouple junctions are disposed, said relatively thin portion of said supporting substrate having a second surface on an opposite side thereof, said layer of said substance being disposed upon said second surface.

17. A sensor as recited in claim 16 further including means for forming a cavity about said first surface of said relatively thin portion of said supporting substrate to isolate said first surface from said fluid and to minimize the conduction of heat therefrom.

18. A sensor as recited in claim 1 wherein said supporting substrate consists of a semiconductor.

19. A method of measuring the concentration of a chemical within the bloodstream of a human body, said method comprising the steps of:
    (a) implanting within the human body a sensor as described in claim 1, said layer of a substance facilitating chemical reactions involving said chemical within the bloodstream;
    (b) measuring the voltage difference signal provided by said wiring means; and
    (c) deriving from said voltage difference signal an indication of the concentration of said chemical within the bloodstream of the human body.

20. The method of claim 19 wherein the chemical for which the concentration is to be measured is glucose and wherein said layer of a substance facilitating chemical reactions is a glucose catalyst.

21. A sensor for providing an electrical voltage representative of the concentration of a chemical dissolved in a fluid, said sensor comprising in combination:
    a. a supporting substrate;
    b. a thin film thermopile disposed upon said supporting substrate, said thin film thermopile including a plurality of pairs of thin film thermocouple junctions disposed upon said supporting substrate, each of said pairs of thermocouple junctions including a reference junction and a sensing junction electrically coupled in series connection with one another and spaced apart form one another, said reference junction and said sensing junction within each pair of thin film thermocouple junctions creating a temperature-dependent voltage when said reference junction and said sensing junction are electrically coupled in series connection, said plurality of pairs of thermocouple junctions being electrically coupled in series connection with one another between first and second terminals;

c. a layer of a substance disposed proximate to each of said sensing junctions, said substance facilitating chemical reactions involving said chemical dissolved in said fluid adjacent said sensing junctions but not adjacent said reference junctions;

d. wiring means coupled to said first and second terminals of said plurality of pairs of thin film thermocouple junctions for providing a voltage difference signal proportional to a difference in temperatures proximate the sensing and reference junctions arising from chemical reactions facilitated by said substance; and e. a catheter having a tip for insertion within a human body, said supporting substrate being secured within said tip of said catheter for being inserted within a human body to measure the concentration of a chemical within body fluid.

22. A sensor for providing an electrical voltage representative of the concentration of a chemical dissolved in a fluid, said sensor operating substantially independently of the absolute temperature of said fluid, said sensor comprising in combination:

a. a supporting substrate;

b. a thin film thermopile disposed upon said supporting substrate, said thin film thermopile including a plurality of pairs of thin film thermocouple junctions, each of said pairs of thermocouple junctions including a reference junction and a sensing junction electrically coupled in series connection with one another and spaced apart from one another, said reference junction and said sensing junction within each pair of thin film thermocouple junctions each creating a temperature-dependent voltage, each such pair of thermocouple junctions creating an electrical potential proportional in magnitude to the temperature difference between the reference junction and the sensing junction thereof, said plurality of pairs of thermocouple junctions being electrically coupled in series connection with one another between first and second terminals to multiply the electrical potential difference created by each such pair of thin film thermocouple junctions;

c. a layer of a substance disposed proximate to each of said sensing junctions but not overlying the reference junctions, said substance facilitating chemical reactions involving said chemical dissolved in said fluid adjacent said sensing junctions but not adjacent said reference junctions; and d. wiring means coupled to said first and second terminals of said thin film thermopile for providing a voltage difference signal proportional to the difference between the temperature proximate the sensing junctions and the temperature proximate the reference junctions arising from chemical reactions facilitated by said substance adjacent said sensing junctions but not adjacent said reference junctions.

23. A method of measuring the concentration of a chemical within a fluid substantially independently of the absolute temperature of the fluid, the method comprising the steps of:

a. placing within the fluid a sensor, the sensor including a thin film thermopile disposed upon a supporting substrate and including a plurality of pairs of thin film thermocouple junctions, each of said pairs of thermocouple junctions including a reference junction and a sensing junction electrically coupled in series connection with one another and spaced apart from one another, said reference junction and said sensing junction within each pair of thin film thermocouple junctions each creating a temperature-dependent voltage, each such pair of thermocouple junctions creating an electrical potential proportional in magnitude to the temperature difference between the reference junction and the sensing junction thereof, said plurality of pairs of thermocouple junctions being electrically coupled in series connection with one another between first and second terminals to multiply the electrical potential difference created by each such pair of thin film thermocouple junctions, the sensor including a layer of a substance disposed proximate to each of said sensing junctions but not overlying the reference junctions, said substance facilitating chemical reactions involving said chemical dissolved in said fluid adjacent said sensing junctions but not adjacent said reference junctions;

b. measuring a voltage difference signal across the first and second terminals of the thin film thermopile to detect the difference between the temperature proximate the sensing junctions and the temperature proximate the reference junction arising from chemical reactions facilitated by said substance adjacent said sensing junction but not adjacent said reference junctions; and c. deriving from said voltage difference signal an indication of the concentration of said chemical within the fluid.

24. A method of measuring the concentration of a chemical within the blood of a living body substantially independently of the absolute temperature of the blood, said method comprising the steps of:

a. contacting the blood of the living body with a sensor, the sensor including a thin film thermopile disposed upon a supporting substrate and including a plurality of pairs of thin film thermocouple junctions, each of said pairs of thermocouple junctions including a reference junction and a sensing junction electrically coupled in series connection with one another and spaced apart from one another, said reference junction and said sensing junction within each pair of thin film thermocouple junctions each creating a temperature-dependent voltage, each such pair of thermocouple junctions creating an electrical potential proportional in magnitude to the temperature difference between the reference junction and the sensing junction thereof, said plurality of pairs of thermocouple junctions being electrically coupled in series connection with one another between first and second terminals to multiply the electrical potential difference created by each such pair of thin film thermocouple junctions, the sensor including a layer of a substance disposed proximate to each of said sensing junctions but not overlying the reference junctions, said substance facilitating chemical reactions involving said chemical dissolved in said blood adjacent said sensing junctions but not adjacent said reference junctions;

b. measuring a voltage difference signal provided by said wiring means; and c. deriving from said voltage difference signal an indication of the concentration of said chemical within the blood of the living body.

* * * * *